United States Patent [19]

Kundu

[11] Patent Number: 4,931,404
[45] Date of Patent: Jun. 5, 1990

[54] METHOD AND DEVICE FOR KETONE MEASUREMENT

[75] Inventor: Samar K. Kundu, Libertyville, Ill.

[73] Assignee: Abbott Laboratories, North Chicago, Ill.

[21] Appl. No.: 944,793

[22] Filed: Dec. 22, 1986

[51] Int. Cl.⁵ .................. G01N 30/00; G01N 33/497
[52] U.S. Cl. ...................................... 436/128; 422/58; 422/61; 422/85; 422/86; 436/130
[58] Field of Search .................. 436/128, 130; 422/58, 422/61, 85, 86

[56] References Cited

U.S. PATENT DOCUMENTS

| | | | |
|---|---|---|---|
| 2,186,902 | 1/1940 | Fortune | 436/130 |
| 2,283,262 | 5/1942 | Kamlet | |
| 4,114,422 | 9/1978 | Hutson | 436/130 |
| 4,397,956 | 8/1983 | Maggio | 436/130 X |
| 4,579,826 | 4/1986 | Bolton et al. | 436/132 |

FOREIGN PATENT DOCUMENTS 850155  8/1970  Canada .

OTHER PUBLICATIONS

Crofford et al., *Trans. Amer. Clin. Climatol. Assoc.*, 88, 128 (1977).
Dubowski, *Clin. Chem.*, 20, 966–972 (1974).
Eriksen, *New Scientist*, 381, 608 (1964).
Freund, *Metabolism*, 14, 985–990 (1965).
Goschke et al., *Resp. Exp. Med.*, 165, 223–244 (1975).
Greenburg et al., *J. Biol. Chem.*, vol. 154–155, 177 (1944).
Krotoszynski et al., *J. Chrom. Sci.*, 15, 239 (1977).
Reichard et al., *J. Clin. Invest.*, 63, 619–626 (1979).
Rooth et al., *The Lancet*, 1102–1105 (1966), 11/19/66.
Rooth et al., *Acta. Med. Scand.*, vol. 187, pp. 455–463 (1970).
Walther et al., *Acta Biol. Med. Germ.*, 22, 117–121 (1969).
Wynn et al., *The Lancet*, 482 (1985), 3/2/85.

*Primary Examiner*—Robert J. Warden
*Assistant Examiner*—Jill Johnston
*Attorney, Agent, or Firm*—Donald L. Corneglio; Thomas D. Brainard; Jeffrey S. Sharp

[57] ABSTRACT

The present invention relates to methods and materials for the detection of ketone and aldehyde analytes in fluid samples by means of reacting analyte containing samples with a matrix comprising a hydrazine compound coupled to an $H^+$ ion exchange resin to produce a hydrazone reaction product with a characteristic color. Methods are also provided for ascertaining the fat catabolism effects of a weight loss dietary regimen comprising determining the breath acetone concentration of the subject by means of contacting said breath with a device comprising an $H^+$ ion exchange resin to which a hydrazine compound has been coupled and correlating the breath acetone concentration to a standard reflecting the effect on breath acetone of fixed rates of fat metabolism.

16 Claims, 4 Drawing Sheets

METHOD AND DEVICE FOR KETONE MEASUREMENT

BACKGROUND

The present invention relates generally to methods and materials for the detection of ketones and aldehydes in fluid (liquid or vapor) samples. The invention is particularly directed to the quantitative determination of ketone and aldehyde concentrations in physiological fluids including blood, urine and breath samples. The invention further relates to methods and materials for monitoring the effects of diet, exercise and diabetic conditions through the quantitative measurement of breath acetone levels.

It is known that "ketone bodies" by which term is generally meant acetone, acetoacetic acid and $\beta$-hydroxybutyric acid, tend to accumulate in the blood stream during periods of relative or absolute carbohydrate deprivation due to the breakdown of storage triglycerides. The process through which overproduction of ketone bodies occurs is not well defined but is related to increased oxidation of long chain fatty acids by the liver. Specifically, acetoacetic acid and $\beta$-hydroxybutyric acid are formed by the liver as intermediates during the oxidation of fatty acid molecules by acetoacetyl coenzyme A. Acetone is formed from the spontaneous decarboxylation of acetoacetic acid. Under normal conditions the intermediate products are further degraded to carbon dioxide and water and the ketone products do not appear at significant concentrations in the bloodstream. Nevertheless, certain metabolic and disease states interfere with the normal degradation of these intermediates which then accumulate in the bloodstream as a result.

The quantitative measurement of serum ketone levels is important because of the relationship between elevated serum ketone body levels and clinical conditions such as diabetes, disorders of the digestive organs, renal insufficiency, uremia and malignant carcinoma. In the course of these disorders, ketone bodies pass into the blood stream and a state of metabolic acidosis (ketosis) occurs. Monitoring for the onset of ketosis is of particular importance in the maintenance of diabetics because the occurrence of ketosis may indicate the need for modification of insulin dosage or other disease management.

The concentration and identity of various ketone and aldehyde components present in the serum may be determined by direct chemical or chromatographic analysis. While such direct analysis provides the most accurate determination of serum ketone and aldehyde concentrations it suffers from numerous deficiencies including the requirement that blood be drawn to provide serum for analysis. Moreover, the analysis must be carried out promptly due to decomposition of acetoacetic acid to acetone during storage. In addition, the analysis of blood serum for ketones and aldehydes by chemical means requires the use of various reagents and procedures which can be complex and inconvenient for consumer use. Further, the use of certain chromatographic techniques such as gas chromatography is often impractical for consumer and many types of professional use.

As a consequence of the limitations of measuring serum ketone and aldehyde levels directly, a large body of art has developed directed to the testing of urine particularly for the presence of ketones. It is known that the concentration of ketones in urine bears an imperfect relationship to serum ketone concentrations. While urine ketone concentrations depend on numerous factors and are not always directly proportional to serum ketone concentrations, testing of urine for ketones is a simple and relatively inexpensive means of monitoring serum ketone concentrations. Such methods are in widespread use by diabetics in both home and clinical settings.

A number of test devices and methods for the determination of urine ketone concentrations are known to the art. Some assays utilize the reaction of acetone with salicylaldehyde in alkaline solution to give the deeply colored orange to red compound salicylalacetone. Any acetoacetic acid in such solutions is converted by the alkali to acetone which further contributes to the color reaction.

Kamlet, U.S. Pat. No. 2,283,262 discloses compositions for the detection of acetone and acetoacetic acid in solutions such as urine. The materials comprise a dry mixture of a member of the group consisting of the alkali metal and alkali-earth metal bisulfite addition products of salicylaldehyde and a member of the group consisting of the alkali metal and alkali-earth metal oxides and hydroxides.

Many assays take advantage of the "Legal" method which utilizes the reaction of a ketone or aldehyde with a nitroprusside (nitroferricyanide) salt in the presence of an amine to form a colored complex. While acetone will react, albeit slowly, with nitroprusside under aqueous conditions, the reaction of acetoacetic acid is some 100 to 200 times faster with the result that "Legal" reactions under aqueous conditions whether detecting "acetone," "acetone bodies" or "ketone bodies" primarily detect acetoacetic acid. The color reaction is believed to occur as a result of a coupling reaction through the nitroso group of the nitroprusside with the ketone or aldehyde to form an intermediate which then complexes with the amine to produce a color characteristic of the specific amine. In forming the complex, the trivalent iron of the nitroprusside is reduced to its divalent state. The color complex, however, is unstable because nitroprusside decomposes rapidly in alkaline solutions. Further, nitroprusside salts are subject to decomposition in the presence of moisture and high pH. Frequently during storage, a brown decomposition product is formed which can interfere with sensitive detection during assays.

While numerous advances and improvements have been made with respect to "Legal" assays for the detection of ketones and aldehydes, such assays are still limited by the instability of nitroprusside at pHs greater than 7. Finally, such assays still measure only the concentrations of ketones in urine and fail to necessarily provide accurate measurements of ketone concentrations in the blood serum.

Of interest to this application is the disclosure of Greenburg, et al., J. Biol. Chem., Vol. 154–155, 177 (1944) which discloses methods for the detection of small amounts of acetone in air and in bodily fluids such as blood and urine. The methods comprise the steps of (1) reacting acetone with 2,4 dinitrophenylhydrazine in a strong acid solution to form the corresponding hydrazone; (2) separating the resulting hydrazone by extraction with carbon tetrachloride and (3) colorimetrically detecting the hydrazone reaction product. Also disclosed by Greenburg, et al., are the properties, that hydrazones, owing to their differential solubilities, may be fractionated with alcohol and that hydrazones give intense colors in solutions of NaOH. Carbon tetrachloride is said to readily extract the yellow colored acetone hydrazone from acid solution while it gives up little upon reextraction with alkali. As a consequence of these solubility characteristics it is said to be possible to eliminate interference from keto acids and to estimate the quantity of acetone hydrazone directly in the carbon tetrachloride. Acetaldehyde 2,4-dinitrophenyl hydrazone is said to be "largely" extracted from carbon tetrachloride by alkali while the concentration of acetaldehyde occurring in the blood causes no interference. Formaldehyde is disclosed to cause no interference because its hydrazone is "completely" extracted by the alkali. The reference further discloses that $\beta$-hydroxybutyric acid present in a fluid sample may be converted to acetone by oxidation with acid dichromate. The reference further discloses that acetoacetic acid may be converted to acetone by acid hydrolysis.

Also of interest to the present invention is the disclosure of Leach, et al., Canadian Patent No. 850,155 which discloses a process for the removal of aldehyde and ketone "impurities" from chemical process streams. The process comprises passing a stream containing aldehyde and ketone "impurities" through a bed of a specially treated weak-acid ion exchange resin. The weak acid ion exchange resin is prepared by treatment with hydrazine or substituted hydrazines such as phenylhydrazine, methylhydrazine and 2,4-dinitrophenylhydrazine wherein the weak acid groups are converted to carboxylic acid salts. The invention is said to be particularly suited to the purification of mono-hydroxy alcohols having from 1 to 15 carbon atoms. Aldehydes and ketones which can be removed by the process are said to include formaldehyde, acetaldehyde, propionaldehyde, isobutyraldehyde, butanone-2, acetone and others.

It is well known in the art that breath samples may be assayed for the presence of acetone in order to determine serum acetone levels. Acetone is a relatively volatile compound having a partition coefficient of approximately 330. It readily diffuses from the blood into the alveolar air of the lungs according to an equilibrium relationship. As a consequence of this equilibrium state, concentrations of acetone in alveolar air are directly proportional to those in the blood and measurements of acetone in alveolar air can be used to determine the concentration of acetone in the serum. Crofford, et al., Trans. Amer. Clin. Climatol. Assoc. 88, 128 (1977).

Current methods for the measurement of breath acetone levels include the use of gas chromatography. Rooth, et al., The Lancet, 1102 (1966) discloses the use of a gas chromatograph capable of detecting acetone at concentrations of 2 to 4 nanomole per liter (nm/1) of air with 18 nm/1 being the concentration for breath of normal individuals. Subjects breathe directly into the device and the acetone peak is read after 40 seconds. Reichard, et al., J. Clin. Invest. 63, 619 (1979) discloses gas chromatographic techniques for the determination of breath acetone concentrations wherein breath samples are collected through the use of a calibrated suction flask into which the test subject breathes through a glass inlet tube. These methods and the instruments required for their use are complicated and expensive and tend to be impractical for use by consumers.

Other methods for the measurement of breath acetone levels involve the use of mass spectrographic equipment. Krotosynski, J. Chrom. Sci., 15, 239 (1977) discloses the use of mass spectrographic equipment in evaluating the ketone content of alveolar air. Twelve ketone components of breath were identified with acetone comprising the major component. Mass spectrographic methods suffer from the same limitations, however, as relate to gas chromatographic techniques.

These various colorimetric methods, such as the Legal method, known for detection of acetone in biological fluids are complex, time consuming and necessitate the use of a spectrophotometer of color charts. Moreover, the methods often require the use of high concentrations of alkali or acids. Methods utilizing a ketone reaction with dinitrophenylhydrazine require the use of strong acid solutions making their use unsuitable for use in the home or in a physician's office. In addition, solutions of hydrazine materials tend to be unstable. Alternative methods for the detection of acetone often require the use of complex and expensive apparatus. There thus continues to exist a need for methods for the quantitative determination of fluid acetone concentrations which are simple, accurate, inexpensive and do not require the use of high concentrations of hazardous reagents.

There exists a desire for methods for the measurement of the rate of fat catabolism. It is a particular problem that many individuals undergoing diets are unable to determine their rate of fat-loss because of daily variation in their body fluid content. Significantly, it is known that early in a diet individuals lose high proportions of fluid as compared to fat. Later in their diets, when individuals may still be catabolizing fat at a constant rate they may cease to lose fluids at the previous high rate or may, if only temporarily, regain fluid weight. The experience of hitting a plateau in weight loss or even regaining weight is psychologically damaging and weakens the subject's resolve to continue with the diet often with the effect that the subject discontinues the diet.

Recently, a method has been disclosed for the determination of daily rate of fat loss. Wynn, et al., Lancet, 482 (1985) discloses that daily fat-loss may be calculated by subtracting daily fluid and protein mass changes from daily weight changes. Changes in body water are estimated from the sum of external sodium and potassium balances and protein mass changes are calculated from nitrogen balances. Such a method is complex and time consuming thus making it inconvenient for the consumer.

One set of methods for measuring body fat is by quantitating total body water (TBW). A number of methods are available for determining TBW. These include isotopic dilution procedures using deuturiated water, tritiated water and $^{18}O$-labelled water. Urine, blood serum or saliva samples are collected after a 2 to 4 hour equilibration. The fluid samples are then vacuum sublimed and the concentration of tracer in the sublimate is determined by mass spectrometer, gas chromatography, or infrared or nuclear magnetic resonance spectroscopy. Body composition can also be measured by a bioelectrical impedance method using a body composition analyzer.

Hydrostatic weighing method is a well known method wherein the subject is completely submerged in a tank of water and the body fat is calculated by taking into account the average density of fat and the amount of water displaced. This method is inconvenient and is still not completely accurate because assumptions must be made relating to non-fat density, lung capacity and other factors. Another method for calculating the percentage of body fat utilizes skin calipers to measure the thickness of fat deposited directly beneath the skin. Pincers are used to measure the thickness of folds of skin and fat at various locations on the body. The results of these measurements are compared with standardized tables to arrive at a figure for percentage of body fat. This method, while more convenient than the use of hydrostatic weighing is less accurate. All methods for determination of body fat content suffer from the fact that they do not reveal the rate of fat loss but only the fat content of the body at a particular time. Because means for determining body fat content are of limited accuracy, means for the determination of the rate of fat loss are similarly limited. Nevertheless it is desired that a simple and convenient method be developed for the determination of the rate of fat-loss wherein such a method is capable of distinguishing weight loss due to loss of fat as opposed to weight loss from the elimination of bodily fluids.

Of interest to the present invention are observations that ketosis occurs in non-diabetic individuals undergoing weight loss through diet, fasting or exercise. Freund, Metabolism 14, 985–990 (1965) observes that breath acetone concentration increases on "fasting." It is disclosed that breath acetone concentrations increased gradually from the end of the first day of the fast to approximately 50 hours into the fast at which time the concentration rose sharply in a linear fashion and reached a plateau on the fourth day. The acetone concentration of the plateau was approximately 300 $\mu$g/liter (5,000 nM) a hundred-fold increase over the normal value of 3 $\mu$g/liter (50 nM). When, instead of fasting, the subject was placed on a "ketogenic" diet with a minimum of 92% of calories derived from fat, the subject suffered a lesser degree of ketosis wherein the plateau had an acetone concentration of approximately 150 $\mu$g/liter (2,500 nM).

Rooth, et al., The Lancet, 1102–1105 (1966) discloses studies relating to the breath acetone concentrations of a number of obese and diabetic subjects. When the caloric intake of three non-diabetic obese subjects was reduced, their breath acetone concentrations as measured by a gas chromatograph increased approximately threefold. On fasting, the subjects' breath acetone concentrations increased to one hundred times normal. Within 16 hours after a heavy meal the subjects' breath acetone concentrations dropped almost to normal. In a study of obese diabetic patients, the authors disclosed evidence that those obese patients who had lost weight in the last three months had higher breath acetone concentrations than those patients who had gained weight.

Walther, et al., Acta Biol. Med. Germ. 22, 117–121 (1969) discloses the results of a study on the effects of continued exercise of a well-trained cyclist. The authors disclose that breath acetone concentration, increases prior to, during and after the cessation of the physical load and reached a maximum 15 to 20 minutes after cessation of the physical load. Breath acetone concentrations approach a normal level one to two hours after the cessation of the physical load. It is suggested that the increased production of acetone is due to the increased utilization of plasma free fatty acids in liver and reduced utilization in peripheral tissue.

More recent studies have shown a correlation between fasting in normal and obese patients and increased blood acetone levels. Rooth, et al., Acta Med Scand. 187, 455–463 (1970); Goschke, et al., Res. Exp. Med. 165, 233–244 (1975); and Reichard et al., J. Clin Invest. 63, 619–626 (1979) all show the development of ketosis in both overweight and normal individuals during fasting. Rooth, et al., (1970) suggests the use of breath ketone measurements as a motivational tool to enforce against dietary cheating. The studies disclose that development of ketosis is slower in overweight than in normal weight individuals. Reichard, et al., discloses that there is a better correlation between breath acetone and plasma ketone concentrations than between urine ketone and plasma ketone concentrations. In addition, Rooth, et al., (1970) discloses that certain urine ketone tests which detect the presence of acetoacetic acid are not entirely reliable because some individuals do not excrete acetoacetic acid in the urine despite increased blood serum concentrations.

Crofford, et al., (1977) discloses the use of breath acetone monitoring for monitoring of diabetic conditions and as a motivational tool in following patients on long-term weight reduction programs. Such monitoring is said to be particularly effective as normalization of the breath acetone is disclosed to occur upon significant dietary indiscretion. Patients' breath samples were monitored using a gas chromatograph and it is suggested that patients be instructed to restrict their caloric input to that which will maintain breath acetone concentrations of approximately 500nM. It is further suggested, though without support, that if breath acetone is controlled at this level and the proper balance of carbohydrate, protein and fat are maintained in the diet that weight loss will occur at a rate of approximately one-half pound per week.

SUMMARY OF THE INVENTION

The present invention relates to improved methods and materials for the detection of ketone and aldehyde analytes in fluid (liquid or vapor) samples. The invention is particularly directed to the quantitative determination of acetone concentrations in physiological fluids including serum, urine and breath samples. The invention is particularly suited for the determination of acetone concentrations. According to one aspect of the invention, methods are disclosed for the quantitative determination of serum acetone concentrations through the measurement of breath acetone concentrations. The method of breath acetone measurement utilizing the methods and materials of this invention is also adoptable for monitoring the insulin dose requirement for Type 1 insulin-dependent diabetic patients and to distinguish between Type 1 (ketotic) and Type 2 (non-ketotic) diabetic patients. Alternatively, concentrations of acetone or other ketones or aldehydes in serum, urine or other liquids may be determined by head space analysis of vapors in equilibrium with a liquid sample. According to further aspects of the present invention, liquid samples may be analyzed quantitatively in a liquid phase reaction for the presence of aldehydes or ketones such as acetoacetic acid. According to still further aspects of the invention, methods are disclosed for ascertaining the fat catabolism effects of a weight loss dietary regimen comprising diet, fasting or exercise through the quantitative determination of serum acetone concentrations. Preferred methods for determination of the rate of fat catabolism comprise measurement of breath acetone concentrations and may be readily determined by utilizing the devices of the invention. The present invention also provides kits for the determination of fluid ketone and aldehyde concentrations and for the determination of the rate of fat catabolism.

Specifically, the invention comprises methods and materials for the determination of fluid ketone and aldehyde analyte concentrations through the reaction of such analytes with a hydrazine compound immobilized on an $H^+$ ion exchange resin to produce a hydrazone reaction product with a characteristic color. The ketone/aldehyde-hydrazone reaction product may then be eluted by means of a solvent from the $H^+$ ion exchange resin and its presence quantitatively determined by detection of a color signal.

Specific methods and configurations of the devices for carrying out those methods are known according to the identity of the analyte of interest and the nature of the sample material to be assayed. When the sample material is a vapor, a fixed quantity of the vapor may be collected by suitable means and the ketone or aldehyde preconcentrated on an adsorbent. The adsorbent for the preconcentration of ketones may be a material such as Tenax TA (a trademark of Enka N.V., Arnham, Netherlands), a 2, 6-diphenyl-p-phenylene oxide polymer or activated silica.

A solvent is then added to desorb aldehydes and ketones such as acetone from the adsorbent and transport the analytes onto a matrix comprising 2,4-dinitrophenyl hydrazine immobilized on an $H+$ ion exchange resin. There, in the acidic environment of the ion exchange resin, the analytes react with the 2,4-dinitrophenyl hydrazine to produce hydrazone reaction products which form color complexes. The hydrazone reaction products may then be eluted from the ion exchange resin by means of a solvent. A known amount of water at an acidic pH is added to the solution to develop the color complexes and their presence is measured quantitatively by means of a spectrophotometer. Because different ketone/aldehyde-hydrazone complexes exhibit differing solubility characteristics, it is possible to selectively extract differing complexes and determine their concentrations individually.

The invention also provides devices for the determination of ketone and aldehyde concentrations in liquid samples. Such devices may utilize head space analysis of vapors in equilibrium with the liquid sample where the samples are volatile aldehydes or ketones such as acetone. Alternatively, liquid samples may be directly assayed by reaction with the hydrazine/$H^+$ ion exchange resins of the invention.

The methods and materials of the present invention may be utilized to monitor diabetic patients, to analyze for various metabolic abnormalities or may be utilized according to one aspect of the present invention for the monitoring of the rate of fat catabolism (fat-loss). It has been found that serum acetone concentrations, and hence alveolar air (breath) acetone concentrations which can be measured by the methods and devices of the present invention, may be correlated directly with the rate of fat catabolism experienced by a subject undergoing a weight loss dietary regimen comprising fasting, dieting, exercise or a combination of the three. Serum and breath acetone concentrations may be determined by a variety of means and the rate of fat-loss calculated therefrom according to the invention. The methods and devices of the invention, however, are extremely convenient, are accurate within about 10% in determining serum acetone levels and are therefore particularly suitable for measuring the rate of actual fat-loss as opposed to determining weight loss which is variable and often reflects variations in fluid losses. By measurement of breath acetone levels, a subject will be able to estimate with a high degree of accuracy his rate of fat-loss, the water-loss/fat-loss ratio and be able to adjust his diet and amount of exercise according to his desired weight loss goals.

DETAILED DESCRIPTION

The present invention comprises methods and materials for the determination of fluid ketone and aldehyde analyte concentrations in both liquid and vapor sample fluids through the reaction of such analytes with a hydrazine such as 2,4-dinitrophenyl hydrazine immobilized on an $H^+$ ion exchange resin to form colored hydrazone reaction products. According to one aspect of the invention, where the fluid to be analyzed is a vapor, a fixed quantity of the vapor may be collected by suitable means and introduced to vapor assay devices for analysis according to the invention.

Figure 1:
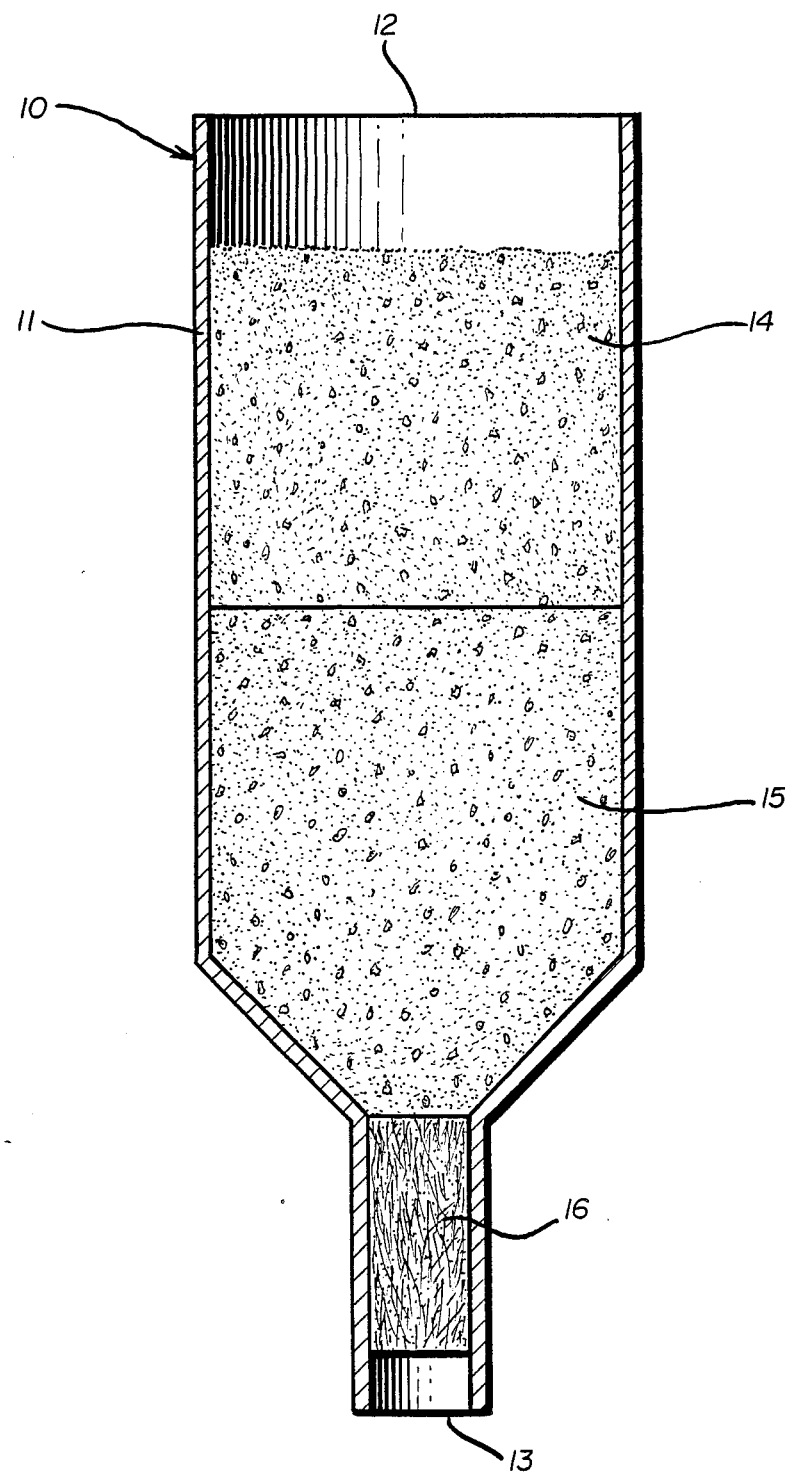
FIG. 1 is a view of a vapor test device of the present invention.

Referring to the drawing, FIG. 1 depicts a vapor test device (10) comprising an inert analyzer column (11) which may be cylindrical, funnel-like or of an alternative configuration having a first end (12) and a second end (13). Within the column is an adsorbent zone (14) which is filled with an adsorbent material capable of selectively adsorbing ketone and aldehyde materials. Below the adsorbent zone (14) is a reaction zone (15) which is filled with an $H^+$ ion exchange resin to which a suitable hydrazine compound has been immobilized. Below the reaction zone (15) and adjacent to the second end (13) is an inert porous barrier material (16) which may be a material such as a porous polyethylene frit, glass wool, nylon fabric, sponge or styrofoam.

Where the sample material to be evaluated is a liquid sample such as urine or serum, head-space vapor assays may be carried out by analysis of vapor in equilibrium with the liquid for the presence of acetone and other volatile ketone components. After collection of a known volume of vapor in equilibrium with the liquid sample, the vapor is analyzed in the same way as breath and other vapor samples. Such head-space analysis is particularly suitable for analysis of the more volatile ketone and aldehyde fractions of samples as such "lighter" fractions such as acetone will be present in the head space vapor in higher proportions than other less volatile "heavy" components.

Quantitative liquid phase assays may also be conducted on liquid samples such as serum or urine according to the present invention. According to such methods, ketone and aldehyde analytes present in liquid samples may be reacted with the hydrazine/$H^+$ ion exchange matrix in means such as a glass test tube, microtitre well or preferably a disposable glass pipette to produce a colored hydrazone reaction product. The colored reaction product may then be extracted with carbon tetrachloride and rinsed with water before being measured at 420 nm on a spectrophotometer.

Reaction Matrix

Hydrazine compounds suitable for use with the present invention include those materials which may be coupled with acidic type ion exchange resins and are capable of reaction with ketones or aldehydes to produce a colored hydrazone reaction product. Suitable hydrazine materials include hydrazines such as phenylhydrazine, methylhydrazine, unsymmetrical diphenylhydrazine, unsymmetrical dimethylhydrazine and 2,4-dinitrophenyl hydrazine. A preferred hydrazine reaction matrix of the invention comprises an $H^+$ type ion exchange resin to which 2,4-dinitrophenyl hydrazine has been associated. The $H^+$ type ion exchange resin provides an environment with pH suitable for reaction of ketones and aldehydes with the hydrazine to form a hydrazone complex.

Suitable $H^+$ type ion exchange resins according to the invention include strongly acidic polymeric particle macroporous ion exchange resins such as those sold under the Amberlite (Rohm and Haas, Philadelphia, PA) and Dowex (Dow Chemical Co., Midland, MI) tradenames. Particularly preferred is the use of $H^+$ type ion exchange resins type AGMP50 and type AG50WX-8 (Bio-Rad, Richmond, CA). The reaction matrix of the invention may be formed by impregnation of a suitable $H^+$ ion exchange resin with a solution of 2,4-dinitrophenyl hydrazine or other hydrazine in solvents such as methanol and water.

EXAMPLE 1

According to this example, Dowex $H^+$ ion exchange resin was impregnated with a solution comprising 0.1% 2,4-dinitrophenyl hydrazine (by weight) in a 1:1 (v/v) solution of methanol and water. The resin and 2,4-dinitrophenyl hydrazine were mixed at room temperature for 15 minutes, filtered, washed thoroughly with water and methanol and dried. The resulting 2,4-dinitrophenyl hydrazine $H^+$ resin was then stored in a cool, dark and dry place until use.

Analyzer Column

Analyzer columns suitable for the present invention comprise inert cylinders or funnels fabricated from a material which will neither react with nor adsorb the analytes and reagents of the present invention. Preferred materials include transparent plastics such as polystyrene and polyethylene terephthalate. Glass tubes are also acceptable but columns fabricated from polyethylene terephthalate are particularly preferred.

Predsorbent Materials

Predsorbent materials suitable for use with the present invention include those materials which are capable of selectively adsorbing ketones and aldehydes from vapor samples. Such materials should also readily and completely desorb ketone analytes in the presence of preferred solvents of the invention such as methanol. Suitable materials include activated silica gel. A particularly preferred material is Tenax TA, a 2,6-diphenyl-p-phenylene oxide polymer (35-60 mesh, Chrompack, Inc. Bridgewater, NJ).

Porous Barriers

Porous barrier materials suitable for use with the present invention include those materials which are inert to ketones and aldehydes, non-reactive with reagents utilized in the invention and are porous with respect to the passage of vapor samples and solvents utilized in devices of the invention. Suitable materials include various porous ceramic and plastic materials with a preferred material being porous polyethylene frits with a pore size of 100 microns (Porex Technologies, Fairburn, GA). Other suitable porous barrier materials include materials such as nylon fabric, glass wool, sponge and styrofoam.

Sample Means

The devices of the present invention for the quantitative detection of ketones and aldehydes in vapor samples require means for the introduction of a fixed quantity of vapor sample to the detection column. Suitable means are those which comprise materials which are inert with respect to the samples and are capable of reproducibly delivering a fixed volume of sample vapor to the device. Balloons and bags are particularly suitable for such applications although it is necessary that the material from which the bag or balloon is constructed be inert to the ketone or aldehyde materials of the sample. It was found that rubberized films and polyvinyl films adsorbed greater than 25% of acetone present in a breath sample in ten minutes. Films found to be suitable included those fashioned from nylon, teflon, very low density polyethylene, and a copolymer of polyester with polyvinyl chloride/vinylidene chloride (Saran). Bolton, et al., U.S. Pat. No. 4,579,826 herein incorporated by reference, describes methods and devices for sampling of predominantly alveolar breath. Bolton, et al. specifically discloses one device comprising a non-self-supporting polymeric tube and a spring means effective to roll the tube upon itself in spiral fashion toward the mouthpiece unit.

Particularly preferred due to its durability, low cost, and high permeability of water vapor is the use of bags of 1 mil thick nylon. According to one embodiment, a nylon bag with a capacity of 450 cubic centimeters is attached to a valve device comprising a column, a mouthpiece, and a plunger. With the plunger set in one position the test subject takes a deep breath, holds it for five seconds and blows a breath sample into the device at a steady rate until the sample bag is completely inflated. The plunger is then pushed down to an alternate position and the sample bag is steadily deflated by a spring means blowing the sample vapor through the device and contacting ketone or aldehyde analytus with either the preadsorbent bed or the reaction matrix. Where the material to be sampled is atmospheric air or an industrial or laboratory vapor sample, a sample port may be substituted for the mouthpiece. Vapor samples may be collected by a bellows or other suitable means and appropriate volumes of material introduced to the device.

Solvents

Suitable solvents must provide an environment in which ketone analytes may react with the hydrazine amine reagents of the invention and where ketones are adsorbed onto preadsorbent materials must be capable of desorbing the ketones and aldehydes and transporting them to the reaction zone. Suitable solvents include lower alcohols with methanol being particularly preferred.

EXAMPLE 2

According to a procedure for use of the device (10) of FIG. 1, a fixed volume of sample vapor is introduced to the first end (12) by suitable sample means and is allowed to flow through the length of the device before it is exhausted from the second end (13). As the sample vapor flows through the device, ketone and aldehyde analytes are adsorbed by the adsorbent material in the adsorbent zone (14). When the volume of the sample vapor has passed through the device (10), a quantity of solvent which is preferably methanol is introduced to the first end of the device (12) which then desorbs ketone and aldehyde analytes adsorbed in the adsorbent zone (14) and transports them to the reaction zone (15). There the ketone and aldehyde analytes react with the immobilized hydrazine to form a characteristic hydrazone product. After a short time period, a sufficient volume of additional solvent is added to the device to elute the hydrazone product. A known amount of slightly acidic water is added in order to develop the color of the hydrazone complex. When the hydrazine is 2,4-dinitrophenyl hydrazine and the analyte is acetone, a yellow color will appear, the intensity of which may be measured at 420 nm on a spectrophotometer.

In order to identify the type of ketone or aldehyde present in a sample, mixtures of ketone-hydrazone complexes may be subjected to selective extraction utilizing solvents such as carbon tetrachloride. According to one procedure, an acetone-dinitrophenyl hydrazone mixture may be extracted with a known volume of carbon tetrachloride by brief mixing. The methanol and carbon tetrachloride separate into two layers and the methanol solution is discarded. The carbon tetrachloride solution is rinsed twice with water and may be centrifuged. The carbon tetrachloride solution is then mixed with a known volume of 0.5 M sodium hydroxide solution which removes any acetaldehyde-hydrazone which might have formed. The carbon tetrachloride solution containing the acetone-hydrazone complex is then again read at 420 nm on the spectrophotometer to determine the amount of acetone present. This last methodology is capable of detecting acetone to a sensitivity limit of 7 nanomoles of acetone per liter in solution.

EXAMPLE 3

According to this example, a quantitative liquid phase assay for the detection of acetone in a test solution was performed according to the methods of the present invention. A 0.05 ml aliquot of a 35 nanomolar solution of acetone in water was added to a pipette containing 1.7 ml of a reaction matrix comprising 2,4-dinitrophenyl hydrazine and an H+ ion exchange resin formed according to the procedure of Example 1. A 1.5 ml aliquot of methanol was then added to the solution and the acetone in solution instantly reacted with the reaction matrix to form a hydrazone reaction product. The reaction product was then eluted off the pipette with methanol, and water (pH 2) was then added. The yellow acetone-hydrazone solution was then read at 420 nm on a spectrophotometer.

The yellow acetone-hydrazone solution was then extracted by addition of carbon tetrachloride and brief mixing therewith. The carbon tetrachloride layer was rinsed twice with water and was read at 420 nm on a spectrophotometer with the intensity dependent on the quality of acetone present in the solution. This test methodology detected the presence of acetone to a sensitivity of 3.5 nm in solution.

MONITORING OF WEIGHT LOSS

In the course of development of the devices of the present invention it was discovered that serum acetone concentrations and hence breath acetone concentrations as measured by the methods and devices of the present invention may be correlated directly with the rate of fat-metabolism (fat-loss) experienced by a subject undergoing a weight loss dietary regimen comprising fasting, dieting, exercise or a combination of the aforesaid.

The invention comprises methods for ascertaining the fat catabolism effects of a weight loss dietary regimen comprising (a) periodically assaying breath for acetone content and (b) correlating breath acetone to a standard reflecting the effect on breath acetone of fixed rates of fat catabolism. A direct correlation between alveolar air (breath) concentrations and the rate of fat-loss has been established. Because breath acetone concentrations are directly proportional to serum acetone concentrations, the correlation between acetone and the rate of fat-loss also holds for serum acetone. References to breath acetone concentrations will therefore, unless otherwise stated, also refer to the serum acetone concentrations which are specifically associated therewith.

Methods for determining the fat catabolism effects of a weight loss dietary program involve the collection of alveolar air (breath) samples and assaying for acetone content. Various methods may be utilized for determination of sample acetone concentrations including mass spectrometry and gas chromatography with preferred methods utilizing the ketone assay devices of the invention. Such assay devices may be provided in which tabular color charts are calibrated to indicate a rate of fat catabolism expressed in suitable units such as pounds of fat catabolized per week. Assay devices comprising a linear reading system may comprise a graphic adjunct such that a color bar scale may be calibrated to indicate a rate of fat catabolism expressed in units such as pounds of fat catabolized per week. Breath may be sampled on a periodic basis such as once daily with samples preferably collected before breakfast in the morning. Breath samples may be taken more frequently than once daily, although samples taken soon after consumption of a meal or after the completion of exercise may indicate lower or higher rates of fat catabolism, respectively, than would be expected to be maintained over a 24 hour period.

EXAMPLE 4

In this example, breath acetone concentrations were measured for a group of dieting individuals and controls utilizing a Shimadzu gas chromatograph (Model GC-8A, Columbia, MD) equipped with a heated gas sampler HGS-2 and a flame ionization detector. The chromatographic column consisted of a 2 meter stainless steel coil, ⅛ inch OD packed with chromosorb 102 3% 80–100 mesh (Supelco, Inc.). The column temperature was maintained at 120° C with ultrapure helium as a carrier gas (5 kg/cm$^2$ pressure). Hydrogen and air pressures were 0.5 kg/cm$^2$ and 0.2 kg/cm$^2$, respectively. The retention time of acetone was 4.2 minutes and the acetone peak was well separated from the methanol, ethanol, isopropanol and acetaldehyde peaks. Calibrations were made by preparing acetone vapor in glass gas jars or from commercially available cylinders containing a compressed air-acetone mixture (Linde Div., Union Carbide). Calibration standards ranging from 4-1000 nm were used to demonstrate a linear relationship between the height of the acetone peak and the concentration of acetone in a sample. A Shimadzu C-3RA integrator was used for calibration purposes.

In order that breath samples taken from different individuals at different times provide accurate and reproducible results, several types of expired breath specimens were tested for acetone concentration. Several types of expired breath samples are suitable for chemical analysis including (1) expired alveolar air; (2) end-tidal air; (3) end-expiratory air and (4) re-breathed air. Mixed expired air is not suitable for breath analysis because it contains variable proportions of alveolar air and dead-space air.

Various types of breath samples were collected from a number of volunteers by methods including (a) end-tidal air by collection of the last part of a big breath; (b) end-expiratory breath specimen by means of a device (Intoximeter, Inc., St. Louis, MO) according to the method of Dubowski, Clin. Chem. 20, 966 (1974) and (c) equilibrated vital capacity air by holding a deep breath for 5 seconds and expelling various fractions of the breath according to the method of Erikson, New Scientist, 381, 608 (1964), the disclosure of which is hereby incorporated by reference. The acetone content of all collected specimens showed differences of less than 2% between the various methods. It was thus concluded that diagnostically useful samples could be obtained simply by holding a deep breath for 5 seconds and expelling the entire breath to obtain a sample of equilibrated vital capacity air. For analysis of breath acetone by gas chromatography, volunteers were asked to take a deep breath, hold for 5 seconds and blow into a silicone coated balloon (1 liter capacity) via a one-way valve and T-connection connected to the gas inlet of a gas chromatograph. After the gas-loop was purged for 10 seconds with a breath sample, a constant volume of 1 cc was allowed to be swept into the chromatographic column for analysis.

EXAMPLE 5

In this example, a diet study was conducted with 170 normal volunteers who were between 0 and 100 pounds above desirable body weight for height according to the Metropolitan Life Height/Weight table. The criteria for selection of volunteers were that they were normal in other respects, had completed a physical examination within the previous 12 months and did not fall into one or more of the following categories: (1) pregnant women; (2) individuals taking lithium salts for depression; (3) individuals with renal or hepatic disease requiring protein restriction; (4) individuals with arteriosclerotic heart disease; (5) diabetics receiving insulin or oral hypoglycimic agents; and (6) individuals with cardiac arrythmias.

The diet program continued for two weeks and the diet included fish, poultry, lean beef, eggs, vegetables, salad, cottage cheese, coffee, tea, sugar free gelatin, and not more than 2 cans of diet soda. Each volunteer was allowed to plan his own daily diet plan, none of which exceeded the limits of 1200 calorie, 40 grams of fat and 40 grams of carbohydrate on any day. Each volunteer also took one multivitamin plus mineral tablet and at least 1500 ml fluid per day.

Breath acetone concentrations of each individual were measured early in the morning before breakfast by gas chromatography according to the procedure of Example 4. Urine concentrations of acetoacetic acid were measured by Ketostix (Miles Laboratories, Elkhart, Indiana). The body weight of each volunteer was also recorded prior to breakfast.

All subjects participating in the program lost between five and ten pounds of body weight in the first week of the diet. The specific amount of weight loss depended on the obesity, gender and level of physical activity of the individual. While it is generally accepted that women in general have lower metabolic rates than men, Wynn, et al., Lancet, 482 (1985), this was confirmed by the study. It was also found that the rate of fat-loss, and hence development of ketosis is dependent on the extent of obesity of an individual, with severely obese individuals losing fat and becoming ketotic at a slower rate than less obese individuals.

It was noted that the rate of fat-loss and increase in breath acetone also depends on individual's physical activity, e.g., a person on a diet and additionally performing physical activity such as aerobics, bicycling or jogging, has a higher breath acetone concentration and rate of fat-loss than one who is on a diet only and not doing any physical exercise.

Figure 2:
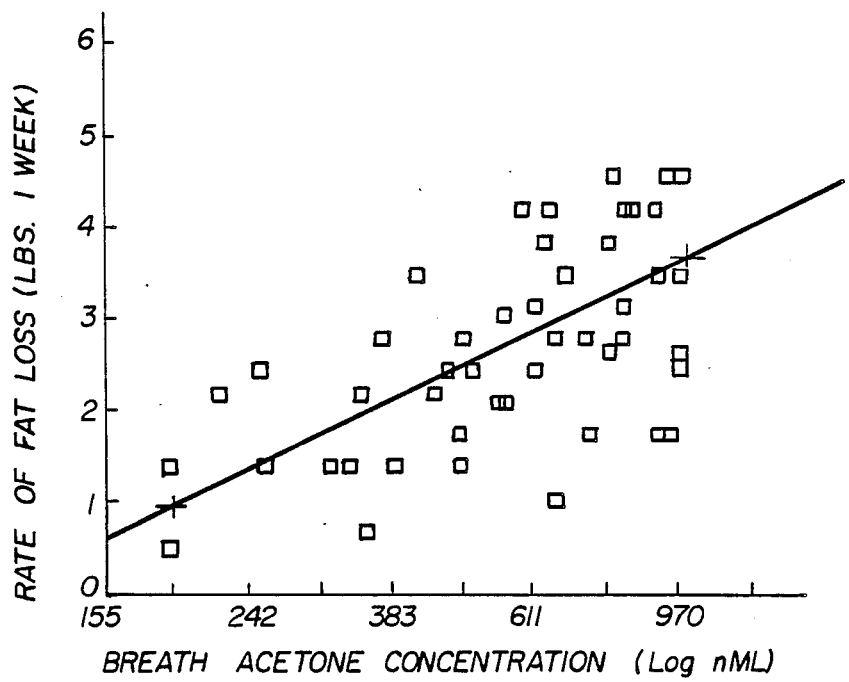
FIG. 2 is a graph illustrating the relationship between breath acetone concentrations and the rate of fat loss corresponding thereto.
Figure 3:
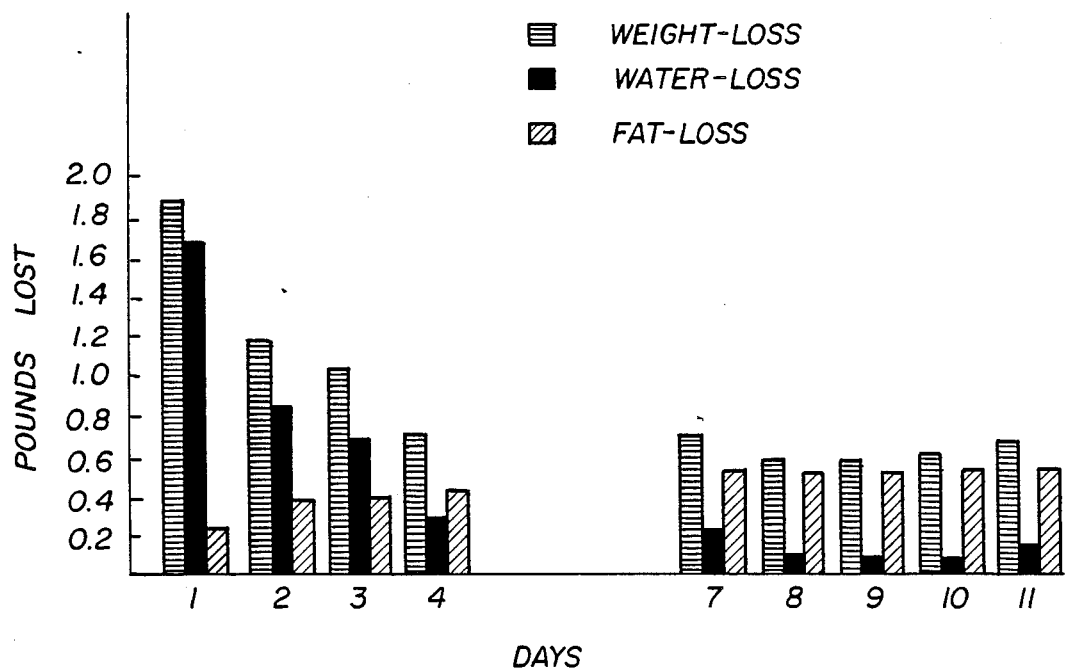
FIG. 3 is a graph illustrating the degree of water and fat loss for dieters 0 to 10 pounds overweight over a period of days.
Figure 4:
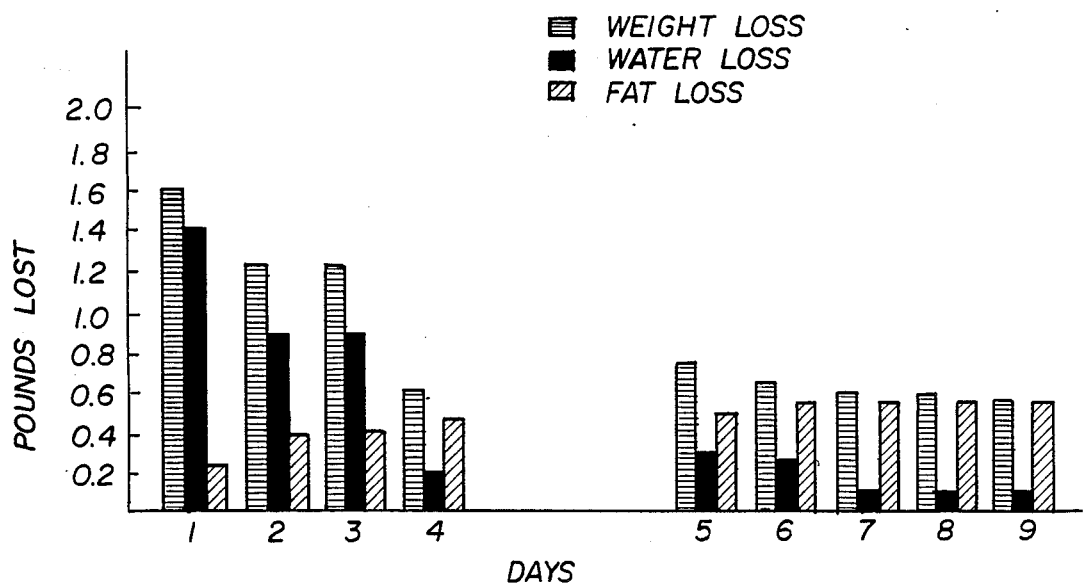
FIG. 4 is a graph illustrating the degree of water and fat loss for dieters 10 to 20 pounds overweight over a period of days.
Figure 5:
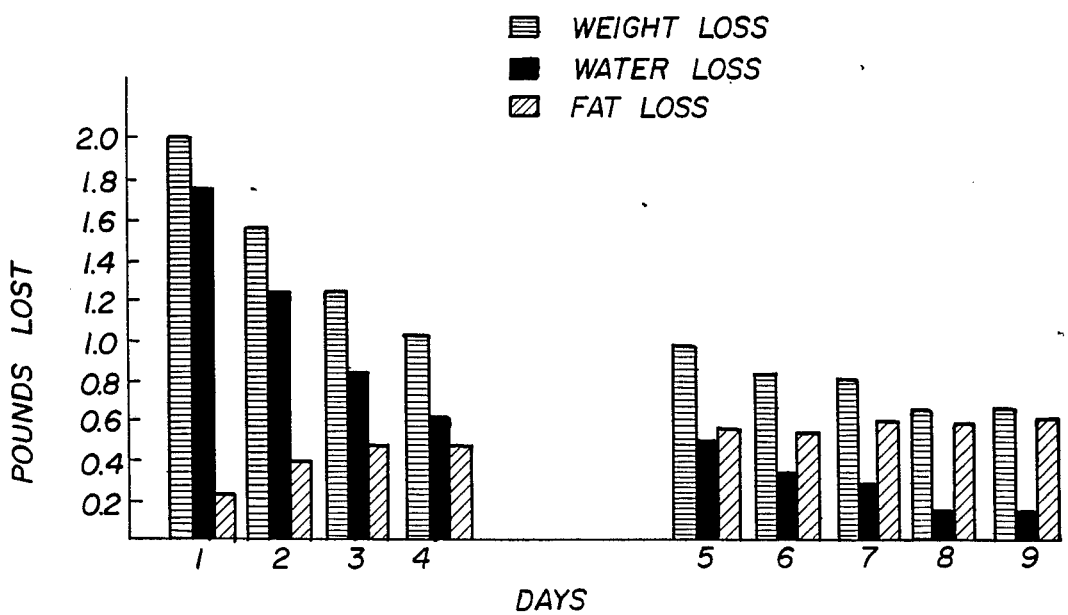
FIG. 5 is a graph illustrating the degree of water and fat loss for dieters 20 to 40 pounds overweight over a period of days.

The relationship between rate of fat-loss and serum/-breath acetone concentration was determined by analysis of the subjects of the example during their second week of dieting. More than 50% of the weight lost in the first week of the diet was due to water loss. By comparison, in the second week of dieting, the amount of water loss for those subjects between 0 and 20 pounds overweight became minimal, approaching 10 to 15% of weight loss, and the loss in body weight was primarily due to fat catabolism. FIG. 2 illustrates the data from individuals between 0 and 20 pounds overweight during the second week of the diet. The "straight line", calculated by linear regression, gives the statistical value of the relation between breath acetone concentration and rate of fat-lossing pounds per week. The relation between breath acetone, fat-loss and calories burned is shown in Table 1 below.

TABLE 1
RELATIONSHIP BETWEEN BREATH ACETONE CONCENTRATION, FAT LOSS AND CALORIE BURNED DURING DIETING

| Breath Acetone[a] Concn. (nM) | Fat-Loss[b] Per Day (lbs) | Per Week (lbs) | Calories Burned[c] Per Day |
|---|---|---|---|
| 8–30 | — | — | — |
| 50 | 0.07 | 0.5 | 286 |
| 67 | 0.14 | 1.0 | 572 |
| 120 | 0.28 | 2.0 | 1144 |
| 212 | 0.43 | 3.0 | 1757 |
| 330 | 0.50 | 3.5 | 2043 |

[a]Breath acetone concentration was calculated by gas chromatography.
[b]Fat-loss was calculated from the slope of the straight line (Shown in FIG. 2)
[c]Calorie burned was devised from the relationship between calories and fat consumption: 1 g fat burned = 9 calorie.

The weight, water and fat-loss profiles of dieters are shown in FIGS. 3 through 6. The values for fat-loss were calculated from the breath acetone measurement and the standard obtained by determination the slope of the straight line in FIG. 2. The values for water-loss were calculated by subtracting from the actual body weight. It should also be noted that in the first week of dieting, the fat-loss figure accounts for the loss of glycogen carbohydrate stores in addition to loss of body fat.

It was found that urine acetoacetic acid has no direct relationship with fat-loss. Although an increase was clearly noted with all dieters after 2 to 3 days of dieting, the increase was not quantitatively related to breath acetone concentrations or to the rate of fat-loss. The blood sugar levels of the dieters did not change during the dieting period.

EXAMPLE 6

In this example, a diet program was conducted for one month with 30 otherwise normal 40–100 pound overweight volunteers. This established that the direct linear relationship between breath acetone and fat-loss exists beyond two weeks using the same low-fat/low carbohydrate diet. The selection of the subjects was the same as in the two-week program except all the subjects had to undergo complete physical examination, laboratory tests including complete blood count, serum chemistries (SMCC 12 or 20) and urinalysis before participation. Breath acetone, urine ketone and body weight of each individual were measured daily and blood sugar level determined weekly. It was noted that volunteers in this group tend to lose water for a longer period of time than less obese people.

Figure 6:
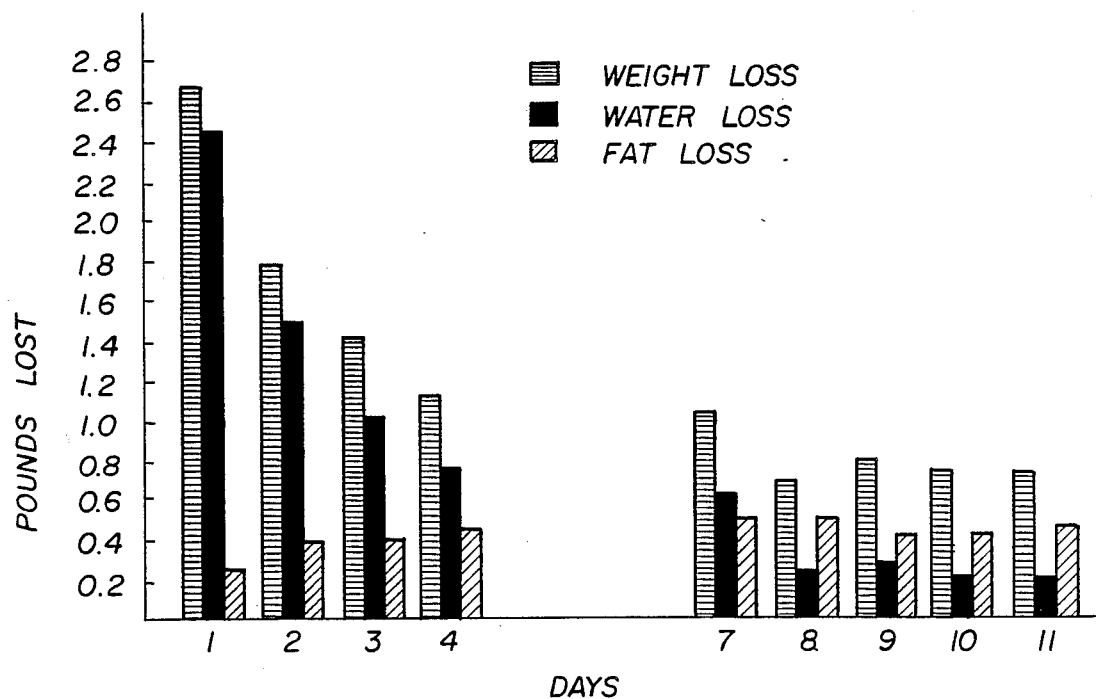
FIG. 6 is a graph illustrating the degree of water and fat loss for dieters 40 to 100 pounds overweight over a period of days.

It was found that for this group, the water-loss becomes minimum (10–15%) in the third week (FIG. 6). It was also found that breath acetone concentrations of subjects in this group were directly proportional to their fat-loss in the third and fourth week as well as in the second week. Although urine acetoacetic acid concentrations of each individual were elevated, there was no direct relationship to the rate of fat-loss. No changes in blood sugar levels were noted.

It is interesting to note that more obese people tend to lose water for a longer period of time. For the group who are between 0–10 pounds overweight, the water-loss becomes minimal (<15%) on day 8, for 10–20 pounds overweight the day shifts to day 9 and for 20–40 pounds overweight it shifts to day 10. People who are between 40–100 pounds overweight, the water-loss continues in the second week of dieting and becomes minimal (<15%) on day 14.

The program also indicated that water-loss in four very obese subjects (100–200 pounds overweight) continues for a much longer time and fluctuates even in the week 4. This group developed ketosis at a slower rate than the other less obese groups and also experienced a lower rate of fat loss.

EXAMPLE 7

In this example, a group of subjects enhanced the extent of their ketosis by participating in physical exercise without decreasing their daily calorie intake. An increase of 20–40% in breath acetone was observed after burning 400–500 calories by physical exercise (bicycle or jogging). Immediately after physical exercise, there was a drop in breath acetone level which then slowly rose after 1 hour and plateaued after 4 to 5 hours.

It was found that ketosis (breath acetone) drops considerably for volunteers when they don't perform exercise on any given day. As a typical illustration, a male subject with a daily intake of 1000 calorie, 30 to 40 grams of fat, and 30 to 40 grams of carbohydrate plateaued at a breath acetone level of 100 nm from the 8th day onwards. He did not perform any rigorous physical exercise. On day 11, he rode on a bicycle for 10 miles at a rate of 10 miles/hr. (500 calorie burned.) It was observed that his breath acetone increased to 250 nm on the next day (day 12). It was found that his breath acetone dropped again to 100 nm when he stopped his physical exercise. This increase in breath acetone in conjunction with exercise suggests that it may be possible to correlate the number of calories burned by exercise with increased breath acetone levels. It has been found that excessive coffee or tea intake also enhances breath acetone production during dieting.

EXAMPLE 8

In this example, the antiketotic effect of dietary "cheating" was measured. It was observed that dieters consuming a high carbohydrate meal by mistake lowered their breath acetone levels appreciably within a few hours. Subjects participating on the diet of Example 7 for 2 weeks or fasting for 12 hours consumed an 8 ounce can of ENSURE (Ross Laboratories, Columbus, OH) containing 250 calories and 36 grams of carbohydrate. The breath acetone of those consuming the product dropped by about 20% after one hour and by about 30% after 3 hours. Similarly, when the test subjects discontinued the diet program and ate a high calorie diet (800 calorie, 100 grams of carbohydrate and 20 to 40 grams fat), a drop of approximately 40% in breath acetone was observed in 5 hours. Within 24 hours, the breath acetone concentration dropped to the pre-diet level.

EXAMPLE 9

In this example, the relationship between development of ketosis (breath acetone) and caloric intake was studies. The results are shown in Table 2 below. As may be observed, the increase in breath acetone is directly proportional to the intake of calories.

TABLE 2

| | EFFECT OF CALORIE INTAKE ON KETOSIS DEVELOPMENT | | |
|---|---|---|---|
| | Breath Acetone Level (times normal ×) | | |
| Calorie Intake[a] | Day 1 | Day 2 | Day 3 |
| 0 | 4× | 16× | — |
| 600–700 | 1.5× | 6× | 13× |
| 1100–1300 | 1.5× | 4× | 8–10× |
| 2000 | 1.1× | 2.4× | 4× |

[a] Diet comprised of high-protein and less than 20 gm carbohydrates/day was used in this study.

Numerous modifications and variations in practice of the invention are expected to occur to those skilled in the art upon consideration of the foregoing descriptions of preferred embodiments thereof. Consequently, only such limitations should be placed on the invention as appear in the following claims.

What is claimed is:

1. A method for the detection of ketone and aldehyde analytes in a fluid sample comprising:
   (a) reacting said analytes with a hydrazine compound coupled to an H+ ion exchange resin to form a colored reaction product,
   (b) fluting said reaction product from the ion exchange resin with a solvent, and
   (c) detecting the presence of a color signal in the eluted material.

2. The method according to claim 1 wherein the hydrazine compound is 2,4-dinitrophenyl hydrazine.

3. The method according to claim 1 wherein the H+ ion exchange resin is a strongly acidic polymeric particle ion exchange resin.

4. The method according to claim 1 wherein the fluid sample is a vapor.

5. The method according to claim 4 wherein the fluid sample is a breath sample.

6. The method according to claim 1 wherein the fluid sample is a liquid.

7. The method according to claim 1 wherein the analyte is acetone.

8. The method according to claim 1 wherein the fluid sample is preconcentrated onto an adsorbent material.

9. The method according to claim 8 wherein the adsorbent material is selected from the group consisting of 2,6-diphenyl-p-phenylene oxide polymers and activated silica.

10. The method according to claim 1 wherein the solvent is selected from the group consisting of lower alcohols.

11. The method according to claim 10 wherein the solvent is methanol.

12. A device for the detection of ketone and alkehyde analytes in a fluid sample comprising an H+ ion exchange resin to which a hydrazine compound has been coupled, and an adsorbent material.

13. A method for ascertaining the fat catabolism effects of a weight loss dietary regimen, said method comprising:
   (a) determining the breath acetone concentration of the subject by (i) contacting said breath with a device comprising an H+ ion exchange resin to which a hydrazine compound has been coupled to form a colored reaction product, (ii) eluting said reaction product from the ion exchange resin with a solvent, and (iii) detecting the presence of a color, and
   (b) correlating the breath acetone concentration to a standard reflecting the effect on breath acetone of fixed rates of fat catabolism.

14. A kit for the detection of ketone and aldehyde analytes in a fluid sample comprising:
   (a) an H+ ion exchange resin to which a hydrazine compound has been coupled;
   (b) a solid adsorbent;
   (c) solvent means for eluting a reaction product from the H+ ion exchange resin; and
   (d) means for detecting the presence of a color signal.

15. The kit according to claim 14 wherein the hydrazine compound is a 2,4-dinitrophenyl hydrazine.

16. A kit for ascertaining the fat catabolism effects of a weight loss dietary regimen comprising:
   (a) means for collecting a fixed volume of breath and contacting it with the solid adsorbent;
   (b) an H+ ion exchange resin to which 2,4-dinitrophenyl hydrazine has been coupled;
   (c) a solid adsorbent;
   (d) means for eluting said reaction
   (e) means for detecting the presence of a color signal; and
   (f) a standard reflecting the effect on breath acetone of fixed rates of fat catabolism.

* * * * *